US007236250B2

(12) United States Patent
Iwai et al.

(10) Patent No.: US 7,236,250 B2
(45) Date of Patent: Jun. 26, 2007

(54) DYNAMIC LIGHT SCATTERING MEASUREMENT APPARATUS USING PHASE MODULATION INTERFERENCE METHOD

(75) Inventors: Toshiaki Iwai, Sapporo (JP); Katsuhiro Ishii, Sapporo (JP)

(73) Assignee: Otsuka Electronics Co., Ltd., Osaka (JP)

( * ) Notice: Subject to any disclaimer, the term of this patent is extended or adjusted under 35 U.S.C. 154(b) by 135 days.

(21) Appl. No.: 10/968,331

(22) Filed: Oct. 20, 2004

(65) Prior Publication Data

US 2005/0122528 A1 Jun. 9, 2005

(30) Foreign Application Priority Data

Oct. 20, 2003 (JP) ............................. 2003-359517

(51) Int. Cl.
*G01B 9/02* (2006.01)
(52) U.S. Cl. ...................................... 356/479
(58) Field of Classification Search ................ 356/479, 356/497
See application file for complete search history.

(56) References Cited

U.S. PATENT DOCUMENTS

| | | | |
|---|---|---|---|
| 4,781,460 A | 11/1988 | Bott | |
| 4,975,237 A | 12/1990 | Watling | |
| 5,434,667 A | 7/1995 | Hutchins et al. | |
| 5,459,570 A * | 10/1995 | Swanson et al. | 356/479 |
| 5,710,630 A * | 1/1998 | Essenpreis et al. | 356/479 |
| 6,198,540 B1 * | 3/2001 | Ueda et al. | 356/479 |

(Continued)

FOREIGN PATENT DOCUMENTS

| | | |
|---|---|---|
| JP | 10-241611 | 11/1998 |
| JP | 2001-066245 | 3/2001 |
| JP | 2003-106979 | 4/2003 |

(Continued)

OTHER PUBLICATIONS

Schmitt et al. "Measurement of optical properties of biological tissues by low-coherence reflectometry". Applied Optics. vol. 32, No. 30, Oct. 20, 1993, pp. 6032-6042.*

(Continued)

*Primary Examiner*—Samuel A. Turner
(74) *Attorney, Agent, or Firm*—Finnegan, Henderson, Farabow, Garrett & Dunner, L.L.P.

(57) ABSTRACT

A dynamic light scattering measurement apparatus using a phase modulation type interference method includes an optical coupler for dividing light from a low coherent light source, a converging lens for irradiating one of the divided lights to a sample 9, phase modulators for modulating the phase of the other divided lights, a spectrum measurement means for measuring a spectrum of the interference light of the phase-modulated reference light and the scattered light outgoing from the sample, and an analyzing means for measuring the dynamic light scattering of particles of the sample based on the first order spectrum corresponding to the basic frequency of the phase-modulating signal or a higher order spectrum corresponding to a frequency equal to two, three or the like times the basic frequency appearing in the interference light spectrum measured by the spectrum measurement means. An amount s/L obtained by normalizing the light path length s within the sample by the mean free path L of the particles is set to be not more than 3. Dynamic properties of a high concentration medium can be measured with high precision based on the scattered light from such medium.

10 Claims, 7 Drawing Sheets

U.S. PATENT DOCUMENTS

| | | | |
|---|---|---|---|
| 6,381,015 B1 * | 4/2002 | Sonehara et al. | 356/497 |
| 6,608,717 B1 * | 8/2003 | Medford et al. | 356/479 |
| 6,738,144 B1 * | 5/2004 | Dogariu | 356/479 |
| 6,982,790 B1 * | 1/2006 | Gershenson | 250/227.19 |
| 2002/0180972 A1 | 12/2002 | Ansari et al. | |

OTHER PUBLICATIONS

R. Yoshida et al., "Heterodyne measurement of power spectra using a low-coherence interferometry," 49th JSAP-RS Proc. (Mar. 2002).

R. Yoshida et al., "Measurements of path-length-resolved spectra of multiply scattered light using a low-coherence interferometer," 63rd JSAP Proc. (Sep. 2002).

K. Ishii et al., "Spectrum analysis of dynamic scattering light measured via a low-coherence interferometer," 19th Congress of the International Commission for Optics, Aug. 25-31, 2002, Firenze, Italy.

Extended Abstracts (The 48th Spring Meeting, Mar. 28, 2001); The Japan Society of Applied Physics and Related Societies No. 3, p. 1008 29-p-P6-3.

* cited by examiner

DYNAMIC LIGHT SCATTERING MEASUREMENT APPARATUS USING PHASE MODULATION INTERFERENCE METHOD

BACKGROUND OF THE INVENTION

1. Field of the Invention

The present invention relates to a dynamic light scattering measurement apparatus capable of performing dynamic light scattering measurement of particles in a sample medium.

2. Description of the Related Art

The dynamic light scattering measurement method is a method for examining dynamic properties of scatterers by irradiating light to a medium such as a suspension and detecting the time fluctuation of the intensity of the scattered light scattered from the scatterers in the medium using a time correlation function and a power spectrum, and this method is widely used for particle diameter measurement, aggregation measurement and the like.

However, this method is used with respect to a diluted medium to which the single scattering theory (a theory that light scattered once can be detected without being scattered again by other particles) is applicable. And therefore, this method has such a disadvantage that, when the concentration of a medium is too high to ignore influences of multiple scattering (a phenomenon that once scattered light strikes other particles and is scattered again), dynamic properties of the particles detected based on the single scattering theory are different from the real dynamic properties.

From this reason, recently, such reports have been made that the time correlation function and the power spectrum of scattered light are measured with using an interferometer having a low coherence light source.

Using such an interferometer having a low coherence light source, only the scattered light component from a specified portion substantially equal to the light path length of a reference light can be extracted, so that only the single-scattered component of scattered light can be selectively detected from a high concentration medium.

Based on this, time-fluctuating spectrum of scattered light and correlation function can be detected, and thereby dynamic properties of particles of a high concentration medium can be measured.

Using the abovementioned interferometer having a low coherent light source, scattered light from particles in the deeper portion of a sample medium can be measured by setting the light path length of the reference light the longer. However, since light decays largely in a high concentration medium, it is not preferable to select so deep a portion in the sample medium.

Consequently, it is requested to establish a standard for setting a suitable range of the light path length of the reference light in order to effectively extract scattered light from a sample medium.

An object of the present invention is to prove that, in the spectrum measurement of a multiple scattering medium, the spectrum of the multiple scattering medium is dependent on the light path length, and thereby to provide a dynamic light scattering measurement apparatus using phase modulation type interference method capable of measuring with high precision the dynamic properties of a high concentration medium based on the scattered light from the high concentration medium.

BRIEF SUMMARY OF THE INVENTION

A dynamic light scattering measurement apparatus according to the present invention includes a low coherence light source, a light path dividing means for dividing light from the low coherence light source, an irradiating means for irradiating one of the lights divided by the light path dividing means to a sample medium, a phase modulation means for modulating the phase of the other of the lights divided by the light path dividing means, a spectrum measurement means for measuring the spectrum of the interference light between the phase-modulated reference light and the scattered light outgoing from the sample medium, and an analyzing means for measuring the dynamic scattering of particles of the sample medium based on the first order spectrum corresponding to the basic frequency of the abovementioned phase-modulating signal or a higher order spectrum corresponding to the frequency equal to two or three times the basic frequency appearing in the interference light spectrum measured by the spectrum measurement means, and the apparatus is characterized in that the amount $s/L$ obtained by normalizing the light path length $s$ within the sample medium by the mean free path $L$ of the particles is set to be not more than 3.

With this structure, the dynamic light scattering of the particles can be measured based on the first order spectrum appearing in the position of the frequency of the phase-modulating signal, the corresponding second order spectrum appearing in the position of two times the frequency of the phase-modulating signal or the corresponding $N^{th}$ order spectrum (N being an integral not less than 1) appearing in the position of N times the frequency of the phase-modulating signal in the interference light spectrum.

In this case, it is necessary to set the range of the light path length $s$ within the sample medium. If the light path length $s$ is set to be not more than three times the mean free path of the particles, the single scattering spectrum component can be efficiently extracted from the multiple scattering spectrum of the sample medium, so that spectrum measurement with high precision can be performed. Therefore, according to the present invention, the amount $s/L$ obtained by normalizing the light path length $s$ within the sample medium by the mean free path $L$ of the particles is limited to be not more than 3.

It is more preferable to set the abovementioned amount $s/L$ obtained by normalizing the light path length $s$ within the sample medium by the mean free path $L$ of the particles to be not more than 2.

The light path length $s$ within the sample medium can be set by adjusting the light path length of the reference light or the fore and aft position of the sample medium. For example, the light path length $s$ can be arbitrarily set by setting at 0 the light path length of the reference light corresponding to the light path length $s$ in the case of a reflected light from the surface of the sample medium being detected and then removing the light path of the reference light or the scattered light from 0.

The abovementioned phase modulation means for modulating the phase of the reference light may be one that modulates the physical length of the light path. In this case, it is necessary to set the amplitude of the light path length modulation by the phase modulation means to be shorter than the coherence length of the abovementioned low coherence light source.

The abovementioned phase modulation means may be one including a mirror and a vibrating element for vibrating this mirror. Further, the abovementioned low coherence light source can be realized by a SLD (Super Luminescent Diode).

A dynamic light scattering measurement apparatus according to the present invention includes a low coherence light source, a light path dividing means for dividing light from the low coherence light source, an irradiating means for irradiating one of the lights divided by the light path dividing means to a sample medium, a phase modulation means for modulating the phase of the other of the lights divided by the light path dividing means, a spectrum measurement means for measuring the spectrum of the interference light between the phase-modulated reference light and the scattered light outgoing from the sample medium, and an analyzing means for measuring the dynamic scattering of particles of the sample medium based on at least either one order number of the first order spectrum corresponding to the basic frequency of the abovementioned phase-modulating signal or a higher order spectrum corresponding to the frequency equal to two, three or the like times the basic frequency appearing in the interference light spectrum measured by the spectrum measurement means, and the apparatus is characterized in that the modulation amplitude of the light path length by the phase modulation means is set to be such a value that the value of the Bessel function corresponding to the order number of the spectrum to be observed becomes substantially the peak.

When a predetermined order number of spectrum corresponding to the phase modulation is requested to be observed, a Fourier series represent the size of the spectrum and the Fourier function is represented by a Bessel function. The value of the Bessel function becomes a function of the modulation amplitude of the light path length. Therefore, the modulation amplitude of the light path length is adjusted so that the value of the Bessel function becomes substantially the largest. Thereby, the predetermined order number of spectrum can be observed with little noise.

The abovementioned phase modulation means may be one that modulates the amplitude of the light path length by a sine wave.

As abovementioned, according to the present invention, by measuring a heterodyne spectrum and fitting the same to the theoretical curve, dynamic properties of the scattering medium can be detected. Further, by limiting the amount s/L obtained by normalizing the light path length s within the sample medium by the mean free path L of the particles to not more than 3, the single scattered spectrum can be efficiently extracted from the sample medium. As a result of this, the width of the spectrum can be measured with high precision and the particle diameter of the scattering medium can be detected.

DETAILED DESCRIPTION OF THE INVENTION

Embodiments of the present invention will be described in detail in the following with reference to the appended drawings.

Figure 1:
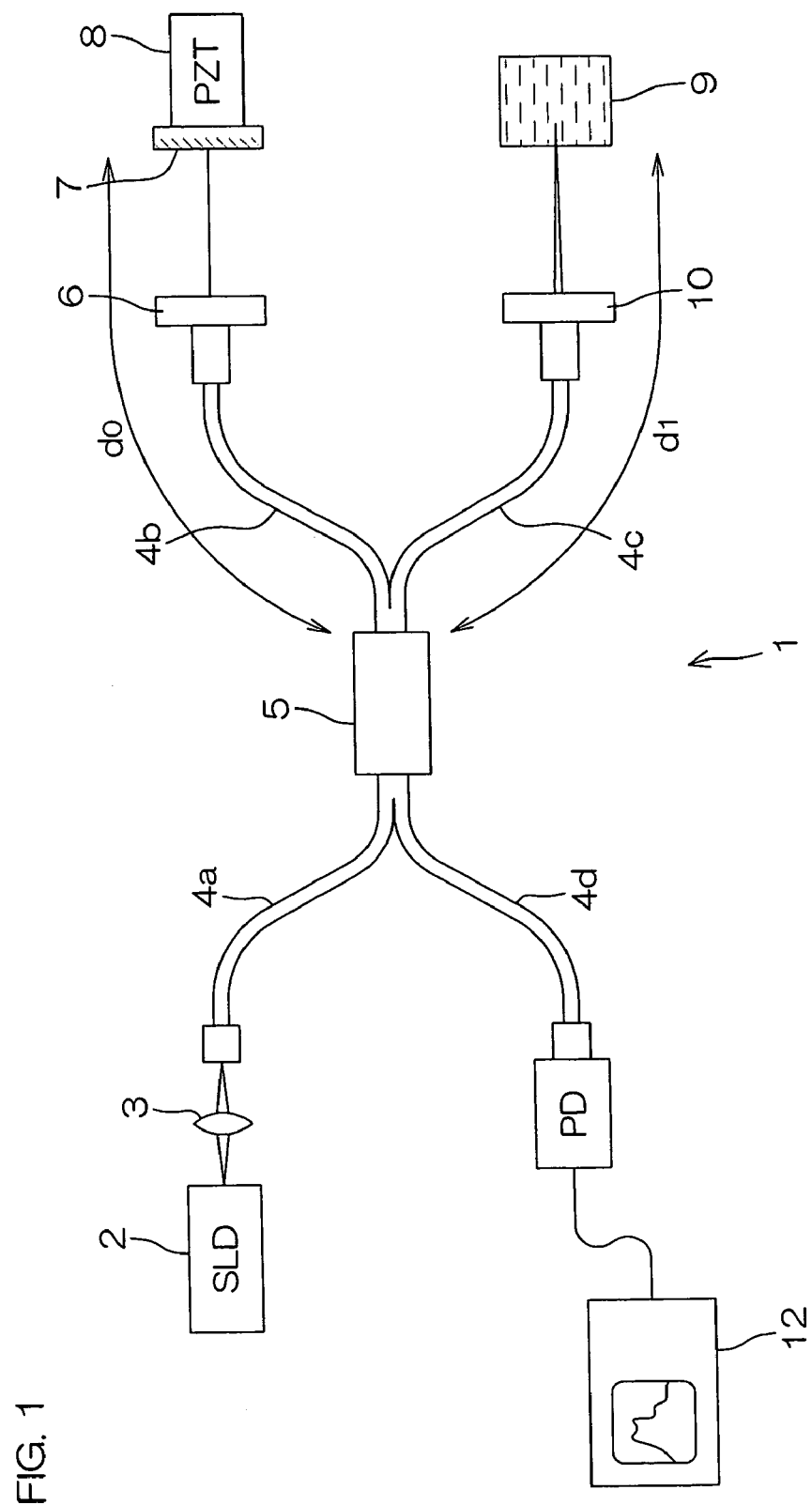
FIG. 1 is a structural view of a dynamic light scattering measurement apparatus using the low coherence interference method according to the present invention.

FIG. 1 is a structural view of a dynamic light scattering measurement apparatus using a Michelson type interferometer according to the present invention.

A low coherence light source (SLD; Super Luminescent Diode) 2 is used as a light source of this dynamic light scattering measurement apparatus 1.

Light from the low coherence light source 2 passes through a lens 3 and enters an optical fiber 4a. After propagated through the optical fiber 4a, the light enters an optical coupler 5 and is divided into two lights by the optical coupler 5. One of the divided lights is passed through an optical fiber 4b, made into parallel light by collimator 6 and reflected by a mirror 7. The reflected light enters the optical fiber 4b again and enters the optical coupler 5. This right is referred to as "reference light". If the one-way path length from the optical coupler 5 to the mirror 7 is represented as $d_0$, the light path length of the reference light is the both-way light path length $2d_0$.

The other light of the lights divided by the optical coupler 5 passes through an optical fiber 4c and is made to enter the scattering medium in a sample cell 9 by a condenser 10. Backward scattered light from the scattering medium passes through the condenser 10 and the optical fiber 4c and enters the optical fiber 5 again. This light is referred to as "scattered light". If the one-way path length from the optical coupler 5 to the sample cell 9 is represented as $d_1$, the light path of the scattered light is the both-way light path length $2d_1$.

The abovementioned reference light and the scattered light entering the optical coupler 5 pass through an optical fiber 4d and enter a light receiving diode (PD; Photo Detector) so that a spectrum analyzer 12 detects power spectrum of the interference intensities of these lights. This spectrum is referred to as "heterodyne spectrum". On the other hand, a power spectrum obtained by interrupting the light path of the reference light and detecting the intensity of only the scattered light is referred to as "homodyne spectrum".

Attached to the abovementiond mirror 7 is a vibrating element 8 for vibrating the mirror 7 to modulate the reference light. It is considered that, by vibration of the vibrating element 8, the mirror 7 is sine-vibrated with the amplitude $\Delta d$ and the angular frequency $\omega_m$.

The vibrating element 8 may comprise, for example, a piezoelectric transducer (PZT). The modulation width is preferably set to be a value shorter than the coherence length of the low coherence light source 2.

Here, first, it is presumed that not the low coherence light source 2 but a perfect coherence light source is used as a light source. The reference light Er is written in a complex representation as $$Er\ ex[2jkd1+j\omega t]$$

and the scattered light Es is written as $$Es\ ex[2jkd2+j\omega t]$$

Er is the amplitude of the reference light; Es is the amplitude of the scattered light; k is the wave number; ω is the vibration frequency of the light; t is time and j is an imaginary part.

The interference light intensity I is represented as $$I = |(Er+Es)|^2$$
$$= |Er|^2 + |Es|^2 + 2ErEs\ \cos[2k(d1-d2)]$$

If frequency modulation exp [$j\omega_m t$] is given to the reference light Er, the interference light intensity I becomes $$I=|Er|^2+|Es|^2+2ErEs\ \cos[2k(d1-d2)+\omega_m t]$$

in which cos [ ] is a section representing interference.

Next, a low coherence light source 2 is used as a light source. The coherence function of the low coherence light source 2 is written as γ(τ). The abovementioned interference light intensity I becomes as follows.

$$I=|Er|^2+|Es|^2+2ErEs\gamma(2(d1-d2)/c)\cos\ [2k(d1-d2)+\omega_m t]$$

in which 2(d1–d2)/c is the time while light is propagated through the difference between the light path lengths of the reference light and the scattered light and this time is written as t'.

$$I=|Er|^2+|Es|^2+2ErEs\gamma(t')\cos[2k(d1-d2)+\omega_m t]$$

In this formula, the section cos [ ] representing interference is multiplied by the coherence function γ of the low coherence light source 2.

Then, it is considered that the scattered light Es time-fluctuates. This fluctuating scattered light Es is represented as Es(t).

Figure 2:
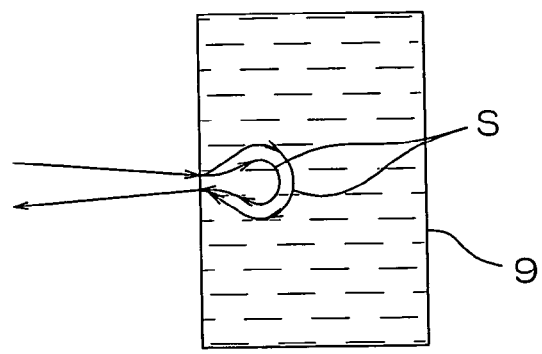
FIG. 2 is a view typically illustrating the light path of a light entering in a light scattering medium in a sample cell.

FIG. 2 is a view typically illustrating the light path of light entering a light scattering medium in a sample cell. The light is multiply scattered by particles in the scattering medium. The light path of the scattered light is written as s. Since the light is multiply scattered, the light path s of the light propagated in the scattering medium is not constant but can take a variety of values from 0 to infinity. If the complex amplitude of the light propagated through the light path length s~(s+ds) is written as Es(t, s)ds, the complex amplitude Es(t) of the scattered light outgoing from the scattering medium is represented by the formula $$Es(t) = \int Es(t, s)ds\ \text{(integration range s=0 to infinity)}$$

The time correlation function Γ(τ) of the interference light intensity I is considered. < > is an operator for taking the time average and * is a complex conjugate operator.

$$\Gamma(\tau) = \langle I(t)I^*(t+\tau)\rangle$$

If this formula is developed, the following formula is obtained (integration range s=0 to infinity).

$$\Gamma(t) = \langle I_r\rangle^2 + 2\langle I_s\rangle\langle I_r\rangle + \langle I_s\rangle^2 \gamma_{I_s}(\tau) + \qquad (1)$$
$$2\langle I_r\rangle \sum_q J_q^2(k\Delta d) \int \langle I_s(s)\rangle |\gamma(t+s/c)|^2 \gamma_{E_s}(\tau, s) ds$$

In this formula, as the time average <Es(t)>=0 of the scattered light Es is used. Ir represents the reference light intensity and Is represents the scattered light intensity. $\gamma_{I_s}(\tau)$ represents the time correlation function of the scattered light intensity. $\gamma_{E_s}(\tau, s)$ represents the time correlation function of the scattered light amplitude Es(t, s).

If the abovementioned formula (1)

is

Fourier-transformed, the power spectrum P (ω) of the interference light intensity I can be obtained. The power spectrum P (ω) of the interference light intensity I is represented by the following formula (2).

$$P(\omega) = 2\pi(\langle I_r\rangle^2 + 2\langle I_s\rangle\langle I_r\rangle)\delta(\omega) + \langle I_s\rangle^2 P_{I_s}(\omega) + \qquad (2)$$
$$2\langle I_r\rangle \sum_q J_q^2(k\Delta d) \int \langle I_s(s)\rangle |\gamma(t+s/c)|^2 P_{E_s}(\omega, s) ds$$

In this formula, ω is the angular frequency of the light; δ(ω) is the delta function; $P_{I_s}$ (ω) is the power spectrum of the scattered light intensity and $P_{E_s}$ (ω, s) is the normalized power spectrum of the scattered light amplitude propagated through the light path length s.

In the abovementioned formula (2) representing the power spectrum P (ω), the first section is a section corresponding to the direct current component of the time correlation function Γ(τ) and it is a value obtained by multiplying the squared value of the mean detected intensity by the delta function δ(ω). The second section is the power spectrum of the whole scattered light intensity that is independent of the light path length of the reference light and is always observed. In the case of multiple scattering, the second section spreads and is hard to observe.

The third section γ(t'+s/c) is the coherence function of the low coherence light source 2 and can be regarded as the delta function δ(t'+s/c) since the width is small. That is, it takes the value 1 when s is such a value that on integrating by s, the relation between the light path length difference (d1–d2) and s becomes t'+s/c=0, and it takes the value 0 when s is any value except that value. Therefore, it is possible to extract the power spectrum of the intensity of the scattered light having a shorter path length difference with respect to the reference light than the coherence length of the light source.

As a result of Fourier development, the Bessel function Jq (kΔd) as a factor is multiplied in the third section. k is the wave number and q is the order number of the Bessel function. q takes such a value as q=0, 1, 2, . . . .

In the abovementioned formula (2), since the central frequency of the power spectrum corresponding to each order number is shifted from the frequency 0 by an amount of modulated frequency of the reference light ±q$\omega_m$, it is possible to measure the power spectrum of the intensity of the scattered light having a shorter path length difference with respect to the reference light than the coherence length of the light source if the modulated frequency $\omega_m$ is sufficiently larger than the band region of the scattered light spectrum.

Figure 3:
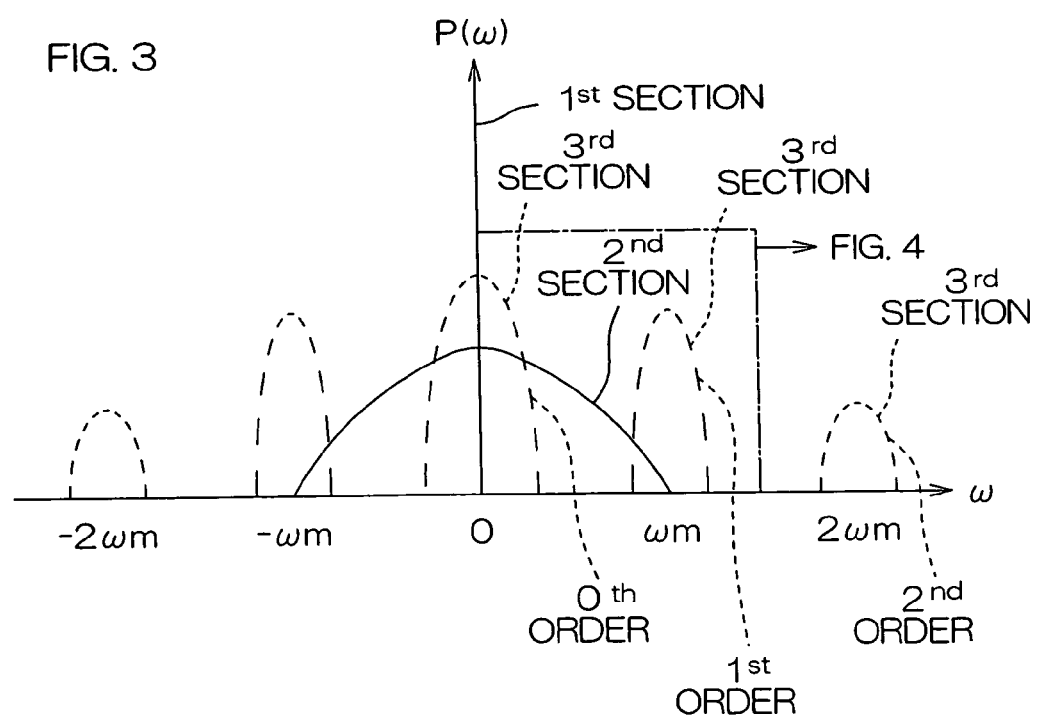
FIG. 3 is a view typically illustrating power spectrum P(ω) of the interference light detected by a spectrum analyzer.

FIG. 3 is a view typically illustrating power spectrum P ($\omega$) of interference light intensity represented by the formula (2), in which the direct current component of the time correlation function of the first section of the formula (2) appears at the position of the frequency $\omega=0$. The power spectrum of the whole scattered light intensity of the second section is distributed with the frequency 0 being as the center. This is shown with solid line in FIG. 3.

The power spectrum of the intensity of the scattered light having a shorter path length difference with respect to the reference light than the coherence length of the light source of every order number of the third section is shown in broken line. There are the spectrum of 0th order near the position of the frequency 0, the spectrum of the first order in the position of the frequency $\omega_m$, the second order spectrum in the position of the frequency $2\omega_m$, the spectrum of -1th order in the position of the frequency $-\omega_m$ and the like.

If the mirror 7 is not vibrated, the power spectrum of the interference light detected by the spectrum analyzer 12 is such that obtained with rendering $\omega_m=0$ in the formula (2). That is, in the graph of FIG. 3, the spectrum has the same shape of the scattered light spectrum of the third section shown in broken line with other spectra than that of 0th order being omitted.

By vibrating the mirror 7 at the frequency $\omega_m$, the first order spectrum of the scattered light, the second order spectrum of the scattered light and the like appear.

The size of this scattered light spectrum is in proportion to the value of the Bessel function Jq (k$\Delta$d) as apparent from the third section of the formula (2). Therefore, if the measurement is carried out in such a condition that the value of the Bessel function Jq (k$\Delta$d) becomes as large as possible, the scattered light spectrum can be clearly observed. For example, when it is desired to clearly observe the first order spectrum of the scattered light, $\Delta$d is set so that the value $J_1$(k$\Delta$d) becomes large. Thereby, the first order spectrum of the scattered light appears to be large without being buried in noises, and consequently errors in observation can be reduced.

Though embodiments of the present invention have been described as above, the present invention is not limited to the abovementioned embodiments. For example, another type interferometer than Michelson type can be used. Further, instead of an interferometer using optical fiber, a space division type interferometer can be also used. A variety of other and further modifications can be performed within the range of the present invention.

EXAMPLE

The power spectrum waveform was measured using a dynamic light scattering measurement apparatus 1 shown in FIG. 1.

Sample cells 9 were respectively filled with suspended water solutions of polystyrene latex. The particle diameters of the polystyrene latex were 450 nm, 1090 nm and 3040 nm, respectively. The concentrations were 1 to 10% by volume respectively to make rather thick medium. The mean free path of the particles in the medium was represented as L. L is a function of the concentration but each L is made L=84 μm by adjusting the concentration of each solution.

A low coherence light source 2 of the wavelength 811 nm, the fluctuation of the wavelength 48 nm and the coherence length 30 μm (a SLD of product number L8414-04 manufactured by HAMAMATU photonics Co. Ltd.) was used. The frequency fm of the sine vibration of the mirror was 2000 Hz and the amplitude $\Delta$d thereof was 0.18 μm.

Figure 4:
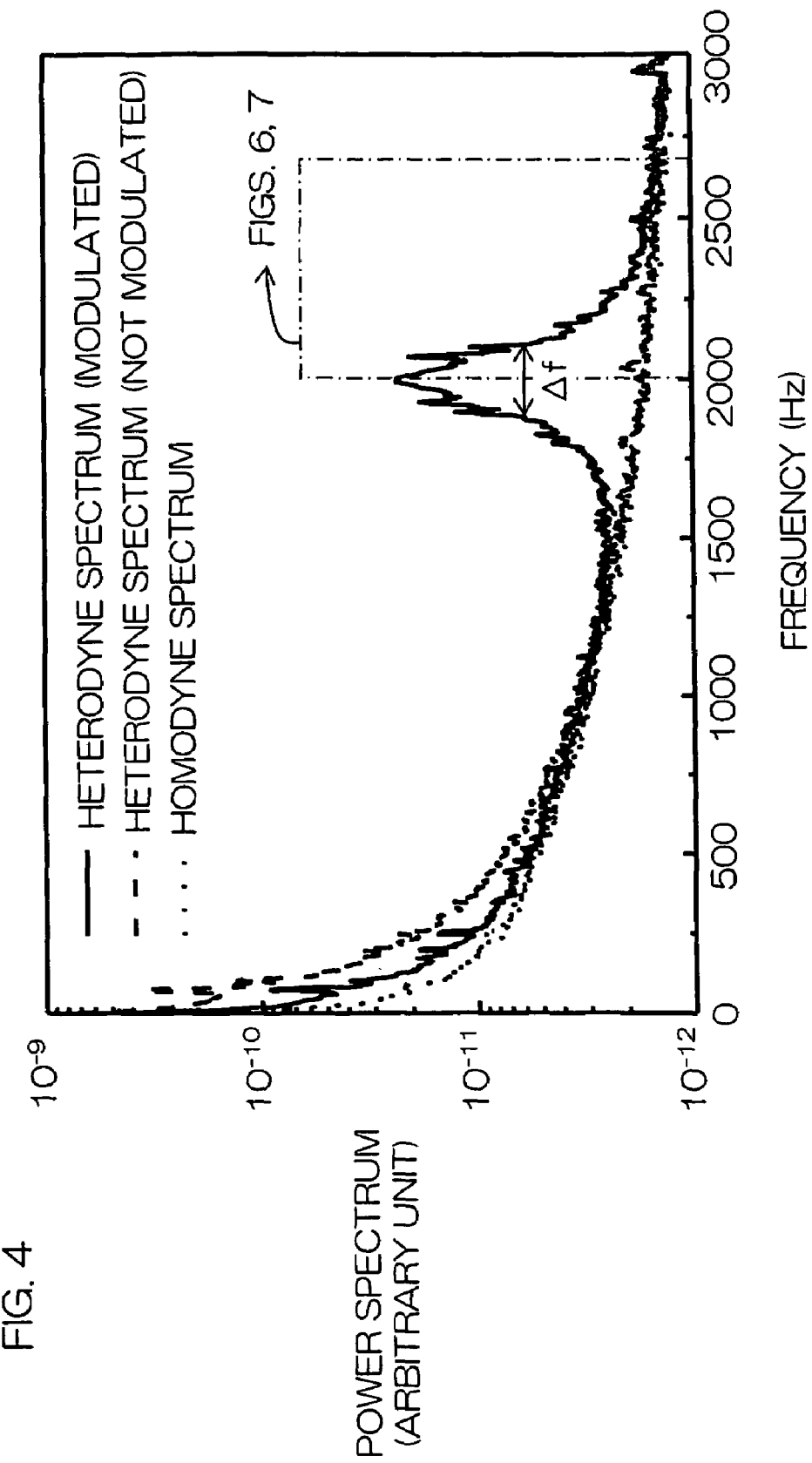
FIG. 4 is a graph showing measured power spectra.

FIG. 4 is a graph showing the measured power spectra. In this figure, shown are a heterodyne spectrum (in a solid line) in the case of making modulation by vibrating the mirror, a heterodyne spectrum (in a broken line) in the case of measuring with keeping the mirror stationary, and a homodyne spectrum (in a dotted line; corresponding to the second section of FIG. 3) in the case of measuring with the reference light being eliminated.

In the heterodyne spectrum (in a solid line) in the case of making modulation, the first order spectrum appears. The half value width $\Delta$f of this first order spectrum was measured.

Figure 5:
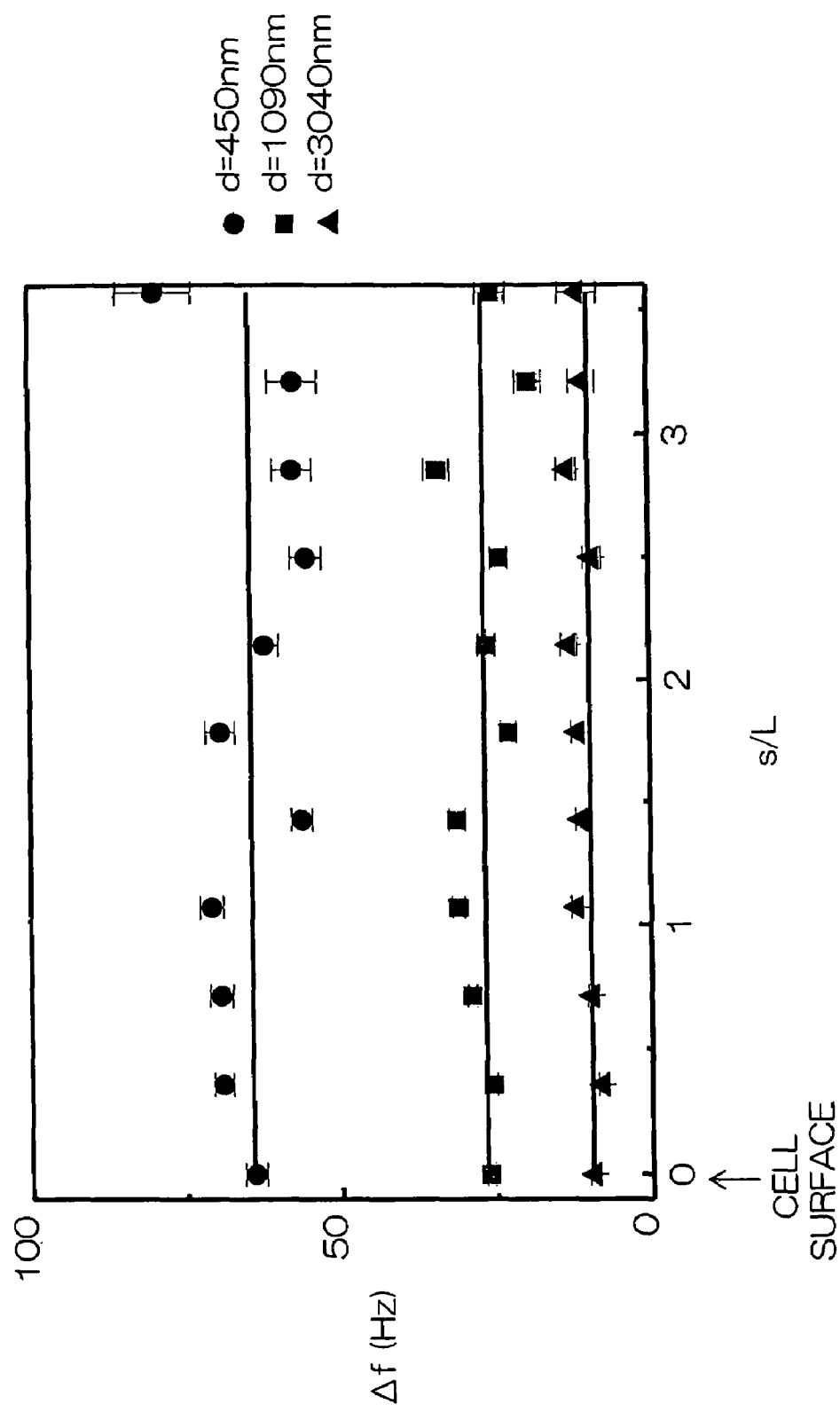
FIG. 5 is a graph in which plotted are the amount normalized by dividing the path length s by the mean free path L of particles as abscissa and the half value width $\Delta f$ as ordinate.

The light path length s within the media was measured on the basis of the distance of displacement of the mirror. If the position of the mirror at which the reflected light from the glass surface of the sample cell 9 is detected is regarded as 0, the light path length s is two times the distance of displacement of the mirror from that position 0. Otherwise, the fore and aft position of the sample media may be adjusted. Plotted were the amount normalized by dividing the light path length s by the mean free path L of a particle as abscissa and the half value width $\Delta$f as ordinate, to obtain the graph of FIG. 5. In FIG. 5, the black circle dots, the squares and the triangles show data of the samples of particle diameters 450 nm, 1090 nm and 3040 nm, respectively.

Whichever particle diameter the particle had, the inclination of the half value width $\Delta$f with respect to change of the normalized light path length s/L was not observed as long as s/L was within 3. If this measurement was influenced by the multiple scattering, the longer the normalized light path length s/L became, the larger the half value width $\Delta$f had to become. Therefore, it proves that this measurement was not influenced by the multiple scattering as long as the light path length s/L was within 3. However, it is presumed that the half value width $\Delta$f becomes large if the light path length s/L is beyond 3.

This graph of measurement of the heterodyne spectrum is tried to fit to the theoretical curve of single scattering. In the case of single scattering model, light entering the cell outgoes therefrom after only once striking on particles in the medium. If the diffusion constant is written as D(this becomes a function of the particle diameter); the scattering vector as q; the scattered light intensity as I and the power spectrum P1 ($\omega$), the theoretical curve of the power spectrum P1 ($\omega$)is represented by the following formula (3). The added letter 1 in the formula (3) represents that this is the first order spectrum.

$$P_1(\omega) = \frac{2\pi I D q^2}{\omega^2 + D q^2} \quad (3)$$

Further, the spread of the frequency $\Delta$fs is represented as $$\Delta fs = Dq^2/2\pi$$

Figure 6:
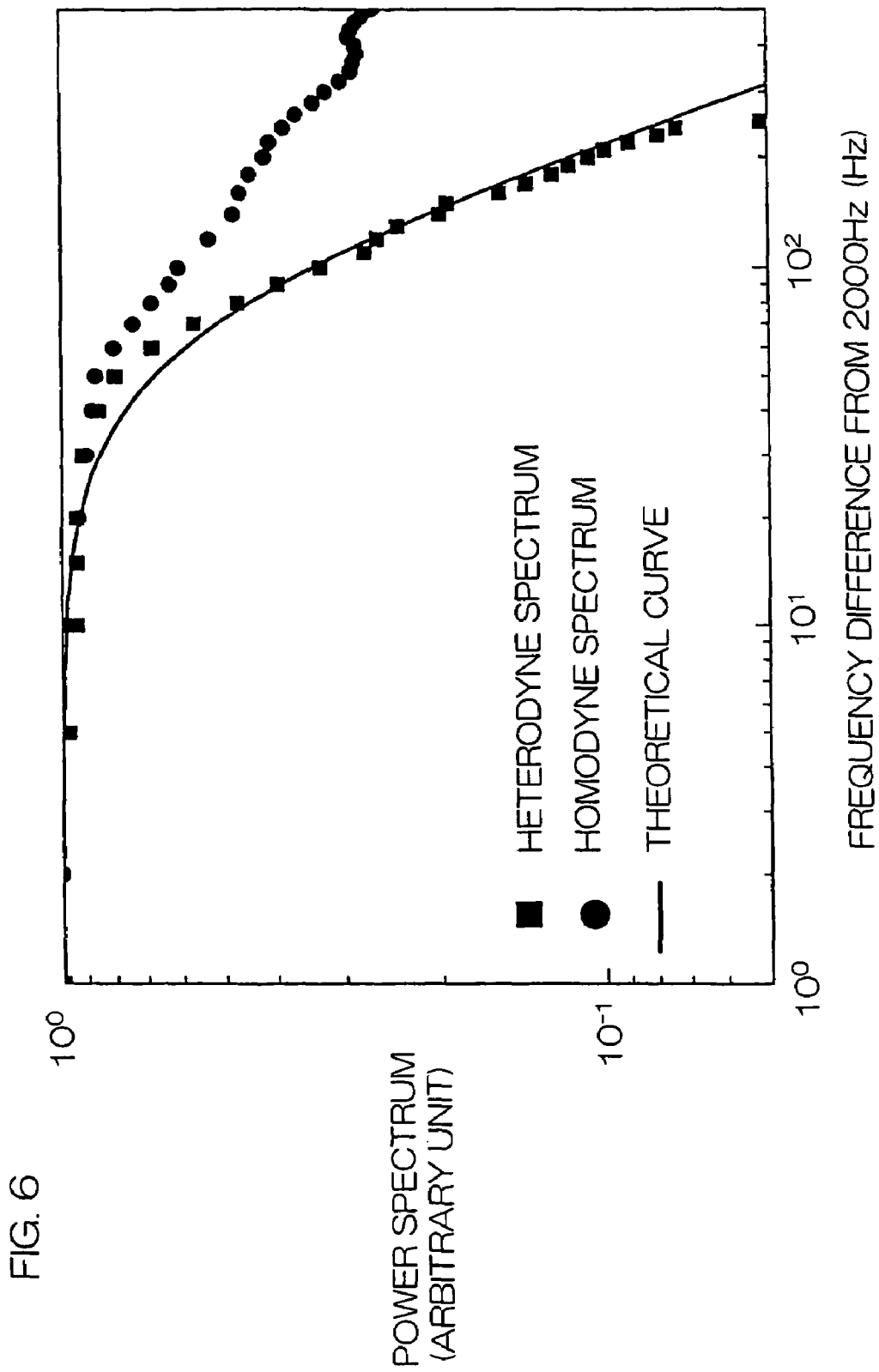
FIG. 6 is a graph in which the heterodyne primary spectrum is plotted on a theoretical curve and the homodyne spectrum is shown for comparison.

FIG. 6 is a graph in which the heterodyne first order spectrum measured near the position s=0 (near the surface of the cell) is plotted on the theoretical curve represented by the formula (3). The homodyne spectrum is plotted in circle dots for comparison. The homodyne spectrum spreads more in comparison with the heterodyne spectrum. This is because the spectrum spreads as a result of multiple scattering. It is observed that the heterodyne spectrum is narrow and well in line with the theoretical curve.

Figure 7:
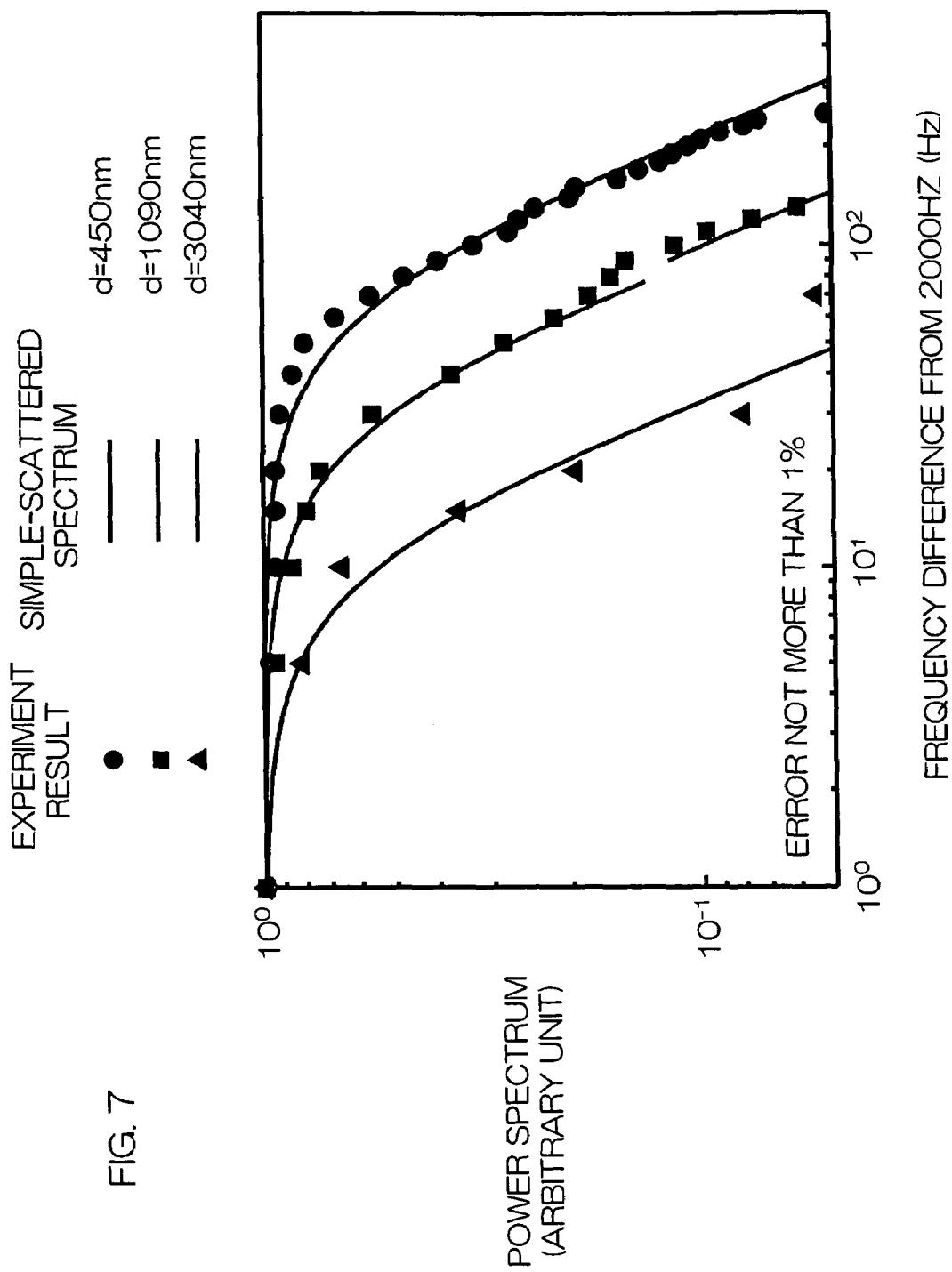
FIG. 7 is a graph in which the heterodyne primary spectrum is plotted on a theoretical curve represented by the formula (3).

FIG. 7 is a graph showing the result of measuring the heterodyne spectrum with changing the particle diameter. In this figure, plotted are the first order heterodyne spectra of the samples of the particle diameters 450 nm, 1090 nm and 3040 nm with black circles, squares and triangles, respectively in this order. The measured first order spectrum well fits to the theoretical curve of single-scattered light to prove that this measurement method can eliminate influences by multiple scattering.

Figure 8:
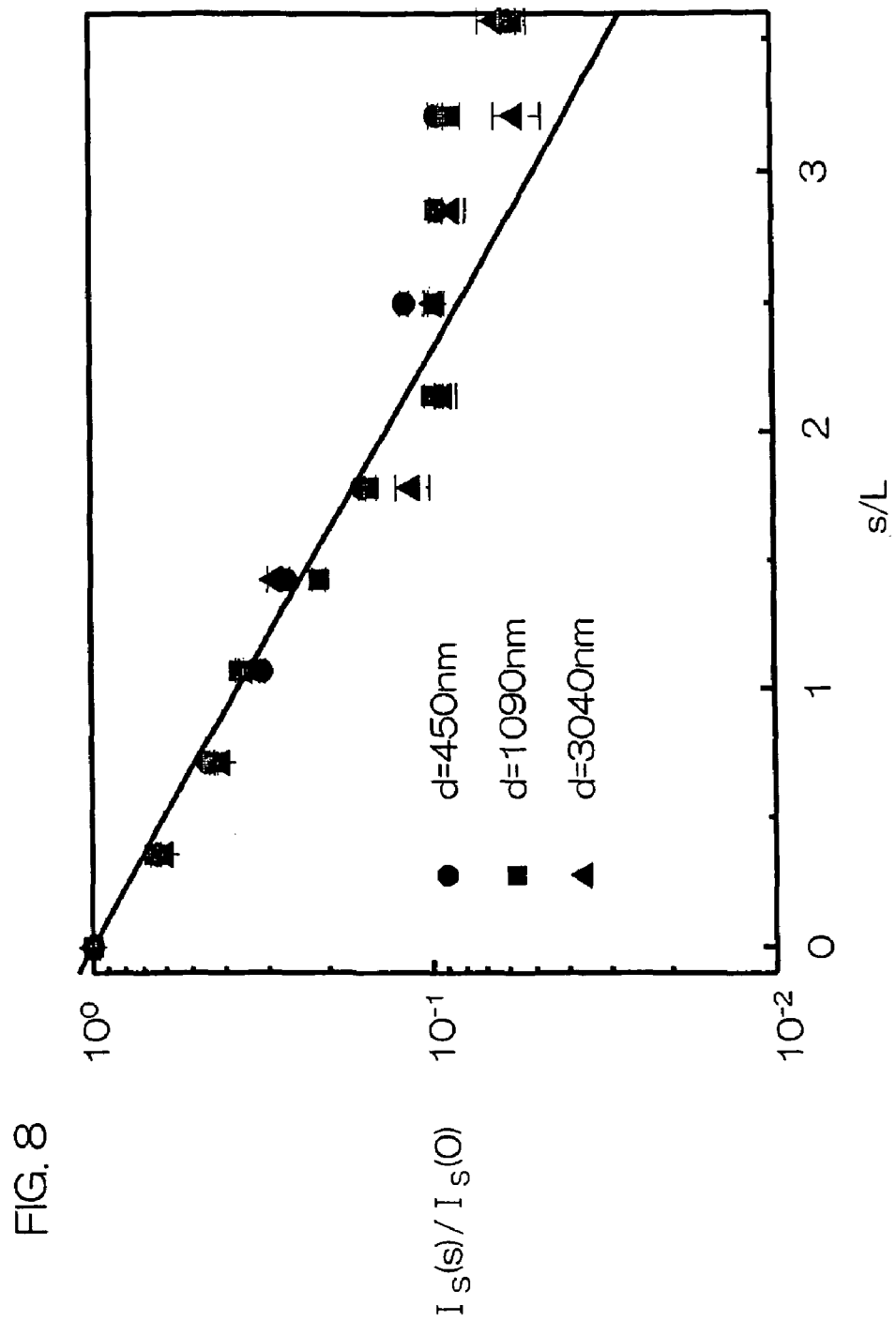
FIG. 8 is a graph obtained by measuring the scattered light intensity $I_s(s)$ of a light propagated through the light path having the length s within the medium, normalizing by dividing the scattered light intensity $I_s(s)$ by the light intensity $I_s(o)$ of the light entering the cell, and plotting the same relative to the abovementioned normalized light path length s/L.

Further, FIG. 8 is a graph obtained by measuring the scattered light intensity $I_s(s)$ of a light propagated on the light path having a length s within the medium, normalizing by dividing the scattered light intensity $I_s(s)$ by the light intensity $I_s(o)$ of the light entering the cell, and plotting the same relative to the abovementioned normalized light path length s/L. Respective $I_s(s)/I_s(o)$ of the samples of the particle diameters 450 nm, 1090 nm and 3040 nm are shown with black circle dots, squares and triangles in this order. Within the range in which s/L is not more than 3, $I_s(s)/I_s(o)$ of the sample of each particle diameter is in line with the theoretical exponential (shown with a straight line in this figure), to prove that influences by multiple scattering could be eliminated. Especially within a range in which s/L is not more than 2, $I_s(s)/I_s(o)$ of the sample of each particle diameter fits well to the theoretical exponential.

What is claimed is:

1. An apparatus for measuring a dynamic light scattering of particles in a sample medium using a phase modulation type interference method,
    comprising a low coherence light source, a light path dividing means for dividing light from the low coherence light source, an irradiating means for irradiating one of the lights divided by the light path dividing means to a sample medium, a phase modulation means for modulating the phase of the other of the lights divided by the light path dividing means, a spectrum measurement means for measuring the spectrum of the interference light between the phase-modulated reference light and scattered light outgoing from the sample medium, and an analyzing means for measuring the dynamic light scattering of particles of the sample medium based on a first order spectrum or a higher order spectrum corresponding to higher harmonics of a basic frequency of a phase-modulating signal appearing in the interference light spectrum measured by the spectrum measurement means, and
    an amount s/L obtained by normalizing a light path length s within the sample medium by a mean free path L of the particles being set to be not more than 3.

2. An apparatus for measuring a dynamic light scattering of particles in a sample medium using a phase modulation type interference method according to claim 1, in which the amount s/L obtained by normalizing the light path length s within the sample medium by the mean free path L of the particles is set to be not more than 2.

3. An apparatus for measuring a dynamic light scattering of particles in a sample medium using a phase modulation type interference method according to claim 1, in which the light path length s within the sample medium is set by adjusting the light path length of the reference light.

4. An apparatus for measuring a dynamic light scattering of particles in a sample medium using a phase modulation type interference method according to claim 1, in which the light path length s within the sample medium is set by adjusting the fore and aft position of the sample medium.

5. An apparatus for measuring a dynamic light scattering of particles in a sample medium using a phase modulation type interference method according to claim 1, in which the phase modulation means modulates the physical length of the light path, and the modulation amplitude of the light path length by the phase modulation means is set to be shorter than the coherence length of the low coherence light source.

6. An apparatus for measuring a dynamic light scattering of particles in a sample medium using a phase modulation type interference method according to claim 1, in which the phase modulation means includes a mirror and a vibration element for vibrating this mirror.

7. An apparatus for measuring a dynamic light scattering of particles in a sample medium using a phase modulation type interference method according to claim 1, in which the low coherence light source is a SLD (Super Luminescent Diode).

8. An apparatus for measuring a dynamic light scattering of particles in a sample medium using a phase modulation type interference method according to claim 1, in which the phase modulation means modulates a physical length of the light path, and
    a modulation amplitude of the light path length by the phase modulation means is set to be such a value that the value of a Bessel function corresponding to the order number of the spectrum to be observed becomes substantially a peak.

9. An apparatus for measuring a dynamic light scattering of particles in a sample medium using a phase modulation type interference method according to claim 1, in which the phase modulation means amplitude-modulates the light path length by a sine wave.

10. An apparatus for measuring a dynamic light scattering of particles in a sample medium using a phase modulation type interference method according to claim 5, in which the phase modulation means includes a mirror and a vibration element for vibrating this mirror.

* * * * *